US006733765B2

(12) United States Patent
Guillou et al.

(10) Patent No.: US 6,733,765 B2
(45) Date of Patent: May 11, 2004

(54) FOAMING COSMETIC CREAM

(75) Inventors: Veronique Guillou, Antony (FR); Jean-Luc Morancais, Ozoir la Ferriere (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/886,216

(22) Filed: Jun. 22, 2001

(65) Prior Publication Data

US 2003/0165455 A1 Sep. 4, 2003

(30) Foreign Application Priority Data

Jun. 23, 2000 (FR) .............................. 00 08085

(51) Int. Cl.$^7$ .................. A61K 7/00; A61K 7/075; A61K 7/50; A61K 7/48
(52) U.S. Cl. .................. 424/401; 510/119; 510/129; 510/130; 510/137; 510/158; 510/159
(58) Field of Search .................. 424/401; 420/4; 510/337, 119, 129, 130, 137, 158, 159

(56) References Cited

U.S. PATENT DOCUMENTS

| | | | | |
|---|---|---|---|---|
| 4,615,819 A | * | 10/1986 | Leng et al. | 510/235 |
| 4,975,218 A | * | 12/1990 | Rosser | 510/137 |
| 5,320,783 A | | 6/1994 | Marin et al. | |
| 5,601,833 A | | 2/1997 | Ribier et al. | |
| 5,629,279 A | | 5/1997 | Erilli et al. | |
| 5,756,108 A | | 5/1998 | Ribier et al. | |
| 5,911,981 A | | 6/1999 | Dahms et al. | |
| 6,007,769 A | * | 12/1999 | Lance-Gomez et al. | 422/4 |
| 6,177,396 B1 | * | 1/2001 | Clapperton et al. | 510/337 |
| 6,299,798 B1 | * | 10/2001 | Guerin et al. | 252/363.5 |

FOREIGN PATENT DOCUMENTS

| | | |
|---|---|---|
| EP | 0 339 994 | 11/1989 |
| EP | 0 598 335 A2 | 5/1994 |
| WO | 99/51716 | 10/1999 |
| WO | WO 01/05932 A1 | 1/2001 |

OTHER PUBLICATIONS

Institute for Surface Chemistry, *Dimeric (Gemini) Surfactants, Novel Surfactants*, vol. 74, (1998), pp. 241–277.
John M. Seddon, *Structure of the Inverted Hexagonal ($H_{II}$) Phase, and Non–Lamellar Phase Transitions of Lipids*, Biochimica et Biphysica Acta, 1031, (1990) 1–69.
Robert G. Laughlin, *The Determination of Phase Diagrams, The Aqueous Phase Behavior of Surfactants*, App. 4, (1996), pp. 521–546.
Sven Engström, *Drug Delivery from Cubic and Other Lipid–Water Phases*, Lipid Technology, vol. 2 No. 2, (Apr. 1990), pp. 42–45.
Glenn H. Brown *Liquid Crystalline Phases in Systems of Amphiphiles, Advances in Liquid Crystals*, vol. 1, (1975), pp. 1–143.
Jean Charvolin, et al., *Les Cristaux De Films, La Recherche 241*, vol. 23, (Mar. 1992), pp. 306–314.
F. Lachampt, et al., *Textures Des Phases Paracristallines*, Revue Française des Corps Gras, No. 2 (Feb. 1969), pp. 87–111.
H.A. Barnes, et al., *Linear Viscoelasticity, An Introduction to Rheology*, vol. 3, (1989), pp. 46–54.
Robert G. Laughlin, *Crystal Solubility: The Kraft Boundary and the Krafft Eutectic, The Aqueous Phase Behavior of Surfactants*, (1996) pp. 106–117.
Par V. Luzzati, et al., *La Structure Des Colloides D'Association. I. Les Phase Liquides Cristallines Des Systemces Emphiphile–Eau*, Acta Cyst, vol. 13, (1960), pp. 660–667.

* cited by examiner

*Primary Examiner*—Shengjun Wang
(74) *Attorney, Agent, or Firm*—Oblon, Spivak, McClelland, Maier & Neustadt, P.C.

(57) ABSTRACT

A composition including a surfactant in an aqueous medium, wherein said surfactant exhibits at least one paracrystalline phase of either a direct type or a cubic type at temperatures varying from 30° C. to 45° C. inclusive.

27 Claims, No Drawings

FOAMING COSMETIC CREAM

BACKGROUND OF THE INVENTION

This application is based on French Patent Application Serial No. 0008085, filed Jun. 23, 2000, which is incorporated herein by reference.

FIELD OF THE INVENTION

The present invention relates to a rinsable foaming composition constituting a cream for topical application, which comprises a specific surfactant system and which exhibits good physical stability up to at least 45° C., and to its use in the cosmetic or dermatological fields, in particular as products for cleaning or removing make-up on the skin, scalp and/or hair.

Cleansing the skin is very important in caring for the face. Cleansing must be as efficient as possible since greasy residues, such as excess sebum, the daily remnants of cosmetic products, and make-up products, in particular waterproof products, accumulate in the skin folds and can block the pores of the skin and result in the appearance of spots.

Several main types of skin cleansing products are known. Foaming detergent aqueous lotions and gels, rinsable cleansing anhydrous oils and gels, and foaming creams.

Rinsable anhydrous oils and gels cleanse by virtue of the oils present in these formulations. These oils make it possible to dissolve fatty residues and to disperse make-up pigments. These products are effective and well tolerated. However, they are disadvantageous in that they are heavy, do not foam, and do not confer a feeling of freshness on application.

Foaming detergent aqueous lotions and gels cleanse by virtue of surfactants, which suspend the fatty residues and the pigments of the make-up products. They are effective and pleasant to use because they foam and because they are easy to remove. However, the lotions are generally fairly fluid, which makes them sometimes tricky to handle, and it is difficult to thicken the gels while retaining good foaming properties.

In order to obtain good foaming performance while having a thick composition, attempts have been made to prepare foaming creams. However, foaming creams are often unstable in heat.

The term "foaming creams" is understood here to mean opaque and viscous compositions often sold in a tube and generally composed of an aqueous medium comprising a mixture of surfactants, such as fatty acid salts (soaps) or anionic, nonionic or amphoteric synthetic surfactants, and of other additives, such as, for example, polymers, polyols or fillers.

These creams, intended in particular for cleansing the skin, foam when they are mixed with water. They can be used in two ways. The first use consists in spreading the cream over the hands, in applying it to the face or to the body, and then massaging it in the presence of water to develop the foam directly on the face or the body. The other possible use of this type of product consists in developing the foam in the palms of the hands before being applied to the face or the body. In both cases, the foam is subsequently rinsed off.

The majority of foaming creams currently available commercially are unstable above 40° C. This means that, if they are stored for a few days at this temperature, they exhibit macroscopic phase separation, resulting in separation into at least two phases. Creams thus phase-separated at a temperature markedly higher than ambient temperature, could be heterogeneous after returning to ambient temperature, and, thus, are unusable because of the deterioration in texture and in the foaming properties. The term "ambient temperature" is understood here to mean a moderate temperature of approximately 20 to 25° C.

It is essential for this type of product to be stable over a wide temperature range. This is because, during its life, the product can be exposed to temperatures ranging from −20° C. to +45° C. at minimum, depending upon the climatic, storage and/or transportation conditions. For example, it is necessary for a cream transported in a car to retain its stability, because of the risk of remaining exposed to the sun for a long period of time, to say at a temperature which can easily reach 50° C. It is also necessary for these foaming creams to be able to be used in hot countries without their transportation and storage presenting a problem.

It is well known that it is possible to prevent phase separation of a foaming cream by increasing the consistency of the product subjected to temperatures of +40° to +45° C. by addition of polymers or of fillers. However, in this case, the product becomes very stiff at moderate ambient temperature and no longer exhibits the properties desired for application to the skin; in particular, it becomes difficult to mix the product with water and to make it foam.

The need thus remains for a foaming cream, stable up to at least 45° C., the cream appearance of which is maintained at ambient temperature even after changing to a higher temperature and which has good foaming characteristics.

DETAILED DESCRIPTION OF THE INVENTION

The inventors have discovered that it is possible to obtain a foaming composition in the form of a cream having good stability, even at temperatures from +40 to +45° C., by using a surfactant system such that at least one para-crystalline phase of direct hexagonal or cubic type appears when the composition is heated to a temperature of greater than 30° C. and such that this paracrystalline phase remains present up to at least 45° C.

The fact that one paracrystalline phase of direct hexagonal or cubic type appears when the composition is heated to a temperature of greater than 30° C. and that this paracrystalline phase remains present up to at least 45° C., means that this phase is present at least at a temperature ranging from 30° C. to 45° C. It is also possible that the paracrystalline phase is present at temperatures above 45° C. In addition, the paracrystalline phase of direct hexagonal or cubic type may be present at higher temperatures, as well.

To obtain the required stability, it is preferable for the paracrystalline phase formed (or liquid crystal) to be of the direct hexagonal phase type. It is not necessary for this paracrystalline phase to be present at ambient temperature but it must appear above a temperature of between 30° C. and 45° C.

Foaming creams which do not exhibit a phase organization as mentioned above are not generally stable at 45° C. At this temperature, they undergo macroscopic phase separation between at least two phases and they are subsequently unsuitable for the desired use when they are again at ambient temperature.

Thus, a subject-matter of the present application is a foaming composition constituting a cream for topical application comprising, in an aqueous medium, a surfactant system such that at least one paracrystalline phase of direct hexagonal and/or cubic type appears when the temperature increases above 30° C. and such that this paracrystalline phase remains present up to at least 45° C.

The obtained composition constitutes a opaque cream which has very good cosmetic properties (softness, creaminess), gives good foam and has good stability for a long time and at elevated temperatures.

The paracrystalline phase or phases present above +30° C. can be of direct hexagonal or cubic type or can be a mixture of these two phases or a mixture of one of these phases or of both these phases with a phase of lamellar type. The paracrystalline phase(s) preferably comprise(s) at least one direct hexagonal phase.

The terms "lamellar phase", "direct hexagonal phase" and "cubic phase" are given, in the present application, the meanings which a person skilled in the art generally gives to them.

Thus, the term "lamellar phase" (phase D according to Ekwall, see Advances in Liquid Crystals, vol. 1, page 1–143, Acad. Press, 1975, edited by G. H. Brown) is understood to mean a liquid crystal phase with plane symmetry comprising several amphiphilic bilayers arranged in parallel and separated by a liquid medium which is generally water.

The term "direct hexagonal phase" (phase F according to Ekwall, see Advances in Liquid Crystals, vol. 1, page 1–143, Acad. Press, 1975, edited by G. H. Brown) is understood to mean a liquid crystal phase corresponding to a hexagonal arrangement of parallel cylinders composed of an amphiphil and separated by a liquid medium which is generally water. In a direct hexagonal phase, the continuous medium is aqueous.

The term "cubic phase" is understood to mean a phase organized in a bipolar manner into separate hydrophilic and lipophilic domains, in close contact which form a thermodynamically stable three-dimensional network with cubic symmetry. Such an organization has been described in particular in "La Recherche", Vol. 23, pp. 306–315, March 1992, and in "Lipid Technology", Vol. 2, No. 2, pp. 42–45, April 1990. Depending upon the arrangement of the hydrophilic and lipophilic domains, the cubic phase is said to be of normal or inverted type. The term "cubic phase" used according to the present invention includes, of course, various types of cubic phases.

A more precise description of these phases can be found in Revue Francaise des Corps Gras, No. 2, February 1969, pp. 87 to 111 (Lachampt and Vila, "Textures des phases paracristallines" [Textures of paracrystalline phases]).

Various techniques can be used to identify the constituent phases of the cream in particular, small-angle and large-angle X-ray diffraction measurements as well as observation by optical microscopy in polarized light.

X-ray Diffraction Technique

The X-ray diffraction technique is one of the most relevant for demonstrating the organization of paracrystalline phases, in particular within a sample. X-ray diffraction measurements can be carried out using a CGR Sigma 2060 generator equipped with an Inel tube comprising a Cu anticathode and a linear focusing chamber installed in symmetrical transmission. The samples are introduced at ambient temperature into a measurement cell closed off by Mylar or Capton windows and placed in a thermally regulated sample holder.

The diffraction spectra obtained with a wavelength $\lambda=1.54$ angstroms (K$\alpha$ line of copper) are recorded using a photostimulable phosphor screen scanned by a Molecular Dynamics PhosphorImager PSI laser scanning module. The detector/sample distance is adjusted to 133 mm, which gives access to lattice distances of between approximately 3 and 110 angstroms. The spectra are recorded at various set temperatures.

With this technique, the paracrystalline phases are characterized by the presence, at small diffraction angles, of a series of several fine lines due to Bragg reflections which correspond to distances: $d1, d2 \ldots dn$ with distance ratios $d1/d1, d1/d2, \ldots, d1/dn$ which are characteristic of each type of phase, as indicated, for example, in "La structure des colloïdes d'association I. Les phases liquides cristallines des systémes amphiphile-eau" [The structure of association colloids, I. The crystalline liquid phases of amphiphile-water systems], V. Luzzati, H. Mustachi, A. Skoulios and F. Husson, Acta Cryst. (1960), 13, 660–667 or in Biochimica et Biophysica Acta (1990), 1031, pp. 1 to 69, by J. M. Seddon. Thus, for a phase with a lamellar structure and in particular for the paracrystalline phase of fluid lamellar type generally denoted by L$\alpha$ and also known as neat phase, the distance ratios are equal to: $1, 2, 3, 4, \ldots$ For the paracrystalline phase of direct hexagonal type generally denoted by H1 or E and also known as middle phase, the distance ratios are equal to: $1, \sqrt{3}, 2, \sqrt{7}, \ldots$ At large diffraction angles, the paracrystalline phases exhibit a band centred over a distance of the order of 4.5 angstroms, whereas the crystalline phases result in fine lines.

Observations By Optical Microscopy

Observations by optical microscopy in polarized light also contribute to the identification of paracrystalline phases, in particular when the number of lines observed by X-ray diffraction is insufficient to unambiguously establish the nature of the paracrystalline phases present.

Optical microscopy observations in polarized light are carried out, for example, using a Laborlux S (Leitz) microscope equipped with an objective with a magnification of 10, with a system of cross polarizers and with a heating stage (Mettler FP80/FP82). The sample is deposited between a microscope slide and a coverglass and covered with a second slide and the assembly is sealed via a Parafilm® seal. The observations are made at various set temperatures or by temperature scanning at 2° C./min between ambient temperature and approximately 95° C.

It is known, for example, that isotropic micellar solutions are non-birefringent, that paracrystalline phases of cubic type are also non-birefringent and that paracrystalline phases of direct or inverted hexagonal fluid lamellar type exhibit, in polarized light, various characteristic textures described, for example, in "Textures des phases paracristallines rencontrées dans les diagrammes d'équilibre: agents de surface, lipides, eau" [Textures of paracrystalline phases encountered in equilibrium diagrams: surfactants, lipids, water], F. Lachampt and R. M. Vila, Revue Francaise des corps gras (1969), 2, 87–111 or in "The aqueous phase behavior of surfactants", Robert G. Laughlin, Academic Press, (1996), pp. 521–546.

Surfactant System

The surfactant system used in the composition of the invention which makes it possible to obtain the appearance of a paracrystalline phase during heating to at least 30° C. preferably comprises at least one water-soluble surfactant and at least one water-insoluble surfactant.

The term "water-soluble surfactant" is understood to mean a surfactant which, at a concentration of 20 g/l in deionized water at a temperature of approximately 25° C., gives a transparent isotropic solution.

Conversely, the term "water-insoluble surfactant" is understood to mean a surfactant which, at a concentration of 20 g/l in deionized water at a temperature of approximately 25° C., gives a cloudy solution, indicating nondissolution of the surfactant in water.

The water-insoluble surfactants form a dispersed phase in the aqueous medium, this dispersed phase comprising all water-insoluble compounds.

Having water-insoluble surfactants allows improvement in the quality of the foam and the creaminess of the composition.

Water-Soluble Surfactants

Any water-soluble surfactant may be used. They are preferably foaming surfactants, that is to say surfactants capable of foaming in the presence of water. They are mainly anionic, nonionic or amphoteric derivatives having sufficiently short fatty chains for these products to be thoroughly soluble at ambient temperature in the aqueous solvent medium of the composition. A water-soluble surfactant or a mixture of such surfactants may be used.

Mention may be made, as water-soluble surfactants, of, for example, anionic surfactants, amphoteric and zwitterionic surfactants, and non-ionic surfactants.

Anionic Surfactants

According to an embodiment of the invention, the surfactant system used preferably comprises at least one water-soluble anionic surfactant and more particularly at least one water-soluble carboxylic acid or one water-soluble carboxylic acid salt, which salt is obtained from the acid and a base. The carboxylic acids which can be used are fatty acids, comprising a saturated or unsaturated linear or branched alkyl chain, having from 6 to 16 carbon atoms and preferably 10 to 14 carbon atoms. The salts of such fatty acids constitute soaps. The fact that the soap is water-soluble or not depends on the length of the alkyl chain and on the counterion constituting the salt. Use may be made, as salts, of, for example, alkali metal salts, alkaline earth metal salts, ammonium salts, aminoalcohol salts and amino acid salts, and in particular of sodium, potassium, magnesium, triethanolamine, N-methylglucamine, lysine and arginine salts. The bases which can be used to produce these salts can, for example, be inorganic bases, such as alkali metal hydroxides (sodium hydroxide and potassium hydroxide), alkaline earth metal hydroxides (magnesium hydroxide) or ammonium hydroxide, or organic bases, such as triethanolamine, N-methylglucamine, lysine and arginine. The carboxylic acid can in particular be lauric acid or myristic acid.

Mention may be made, as water-soluble soap, of, for example, potassium salts of $C_{10}$ to $C_{14}$ fatty acids and in particular the potassium salt of lauric acid, the potassium salt of myristic acid and their mixtures.

Soap is generally introduced into the composition in the form of a base, on the one hand, and of the fatty acid, on the other hand, the formation of the salt taking place in situ. Thus, when the water-soluble soap is composed of the potassium salt of lauric acid and/or of the potassium salt of myristic acid, the composition can then comprise lauric acid and/or myristic acid with a sufficient amount of potassium hydroxide to form the potassium salts of lauric acid and/or of myristic acid.

Mention may be made, as other anionic surfactants which can be used in the composition of the invention as water-soluble surfactant, of, for example, ethoxylated carboxylic acids and their salts; sarcosinates and acylsarconisates and their salts, such as sodium lauroyl sarcosinate; taurates and methyl-taurates and their salts; isethionates and acyl-isethionates, reaction products of fatty acids comprising from 10 to 22 carbon atoms with isethionic acid, and their salts, such as sodium isethionate and sodium cocoyl isethionate; sulphosuccinates and their salts; alkyl sulphates and alkyl ether sulphates and their salts, in particular sodium or triethanolamine lauryl sulphate and sodium or potassium lauryl ether sulphate; monoalkyl and dialkyl esters of phosphoric acid and their salts, such as, for example, sodium mono- and dilauryl phosphate, potassium mono- and dilauryl phosphate, triethanolamine mono- and dilauryl phosphate, sodium mono- and dimyristyl phosphate, potassium mono- and dimyristyl phosphate, diethanolamine mono- and dimyristyl phosphate, or triethanolamine mono- and dimyristyl phosphate; alkane-sulphonates and their salts; bile salts, such as cholates, deoxycholates, taurocholates or taurodeoxy-cholates; lipoamino acids and their salts, such as mono- and disodium acylglutamates; or bipolar geminal surfactants, such as described in Surfactant Science series, Vol. 74, published by Krister Homberg.

Amphoteric and Zwitterionic Surfactants

Mention may be made, as amphoteric or zwitterionic surfactants which can be used as water-soluble surfactants, of, for example, betaines, such as dimethylbetaine, cocobetaine and cocamidopropyl betaine; sulphobetaines, such as cocamidopropyl hydroxysultaine; alkylamphoacetates, such as cocoamphodiacetate; and their mixtures.

Nonionic Surfactants

Mention may be made, as nonionic surfactants capable of being used as water-soluble surfactants, of, for example, polyol ethers comprising fatty chains (8 to 30 carbon atoms), such as oxyethylenated sorbitol or glycerol fatty ethers; polyglycerol ethers and esters; polyoxyethylenated fatty alcohols which are ethers formed of ethylene oxide units and of at least one fatty alcohol chain having from 10 to 22 carbon atoms, the solubility of which depends on the ethylene oxide number and on the length of the fatty chain; for example, for a fatty chain comprising 12 carbon atoms, the ethylene oxide number must be greater than 7, and mention may be made, as examples of polyoxyethylenated fatty alcohols, of lauryl alcohol ethers comprising more than 7 oxyethylene groups; alkyl polyglucosides, the alkyl group for which comprises from 1 to 14 carbon atoms (alkyl-$C_1$–$C_{14}$ polyglucosides), such as, for example, decyl glucoside, lauryl glucoside or cocoyl glucoside; alkyl glucopyranosides and alkyl thioglucopyranosides; alkyl maltosides; alkyl-N-methylglucamides; polyoxyethylenated sorbitan esters which generally comprise from 1 to 100 ethylene glycol units and preferably from 2 to 40 ethylene oxide (OE) units; aminoalcohol esters; and their mixtures.

The surfactant system used in the composition of the invention comprises a content of water-soluble surfactant(s) which can range, for example, from 10 to 50% by weight (as active material), preferably from 15 to 35% by weight, with respect to the total weight of the composition. According to a preferred embodiment of the invention, the surfactant system in the composition of the invention comprises at least 10% by weight, preferably at least 15% by weight and more preferably at least 20% by weight of water-soluble surfactant(s) with respect to the total weight of the composition.

Water-Insoluble Surfactants

The water-insoluble surfactants contribute in particular the texture (consistency) of the final composition. Furthermore, in the temperature range between approximately 25° C. and 45° C., these surfactants partially associate with the water-soluble surfactants to contribute to the formation of the paracrystalline phase (preferably direct hexagonal phase) which is the source of the stability of the product up to at least 45° C.

Mention may in particular be made, as water-insoluble surfactants used in the composition according to the invention, of water-insoluble carboxylic acids and their salts, which salts are obtained from the acid and a base, and thus of water-insoluble soaps, that is to say carboxylic acid salts, comprising a saturated or unsaturated, linear or branched alkyl chain, having from 6 to 30 carbon atoms and preferably 12 to 22 carbon atoms. For the derivatives comprising a single saturated fatty chain, the chain advantageously comprises from 12 to 32 carbon atoms, preferably from 14 to 22 carbon atoms and better still from 16 to 20 carbon atoms. For the derivatives comprising a mono-unsaturated or polyunsaturated or branched fatty chain, the chain advantageously comprises from 16 to 34 carbon atoms and preferably from 18 to 24 carbon atoms.

Mention may in particular be made, as carboxylic acid, of palmitic acid and stearic acid.

Use may be made, as salts, of alkali metal salts, alkaline earth metal salts, the ammonium salts, aminoalcohol salts and amino acid salts, and in particular of the sodium, potassium, magnesium, triethanolamine, N-methylglucamine, lysine and arginine salts. The bases which can be used to produce these salts can, for example, be inorganic bases, such as alkali metal hydroxides (sodium hydroxide and potassium hydroxide), alkaline earth metal hydroxides (magnesium hydroxide) or ammonium hydroxide, or organic bases, such as triethanolamine, N-methylglucamine, lysine and arginine.

Mention may be made, for example, as insoluble soap, of the sodium salt of $C_{12}$ to $C_{22}$ fatty acids and the potassium salt of $C_{16}$ to $C_{22}$ fatty acids and in particular of the potassium salt of palmitic acid and the potassium salt of stearic acid.

The soap is generally introduced into the composition in the form of the base, on the one hand, and of the fatty acid, on the other hand, for formation of the salt taking place in situ. Thus, when the insoluble soap is composed of the potassium salt of palmitic acid and/or of the potassium salt of stearic acid, the composition can then comprise palmitic acid and/or stearic acid with a sufficient amount of potassium hydroxide to form the potassium salts of palmitic acid and/or of stearic acid.

Mention may be made, as other surfactants which can be used in the composition of the invention as insoluble surfactant, of, for example, insoluble nonionic or anionic surfactants, such as esters of glycerol and of fatty acids comprising from 14 to 30 carbon atoms, such as glyceryl stearate; alkyl polyglucosides, the alkyl group for which comprises from 15 to 30 carbon atoms (alkyl-$C_{15}$–$C_{30}$ polyglucosides), such as, for example, cetostearyl glucoside; optionally oxyethylenated sterol and phytosterol derivatives; alkaline salts of cholesterol sulphate and in particular the sodium salt; alkaline salts of cholesterol phosphate and in particular the sodium salt; polyoxyethylenated fatty alcohols comprising an oxyethylene chain having a small number of oxyethylene groups and in particular less than 10 oxyethylene groups; dialkyl phosphates, such as alkaline salts of dicetyl phosphate and in particular the sodium and potassium salts; alkaline salts of dimyristyl phosphate and in particular the sodium and potassium salts; lecithins; sphingomyelins; ceramides and their mixtures.

The surfactant system used in the composition of the invention preferably comprises a content of water-insoluble surfactant(s) ranging from 5 to 50% (as active material) and preferably from 5 to 30% by weight with respect to the total weight of the composition.

The surfactant system (water-soluble and insoluble surfactants) is present in the composition of the invention in an amount, as active material, which can range, for example, from 20 to 65% by weight and preferably ranges from 30 to 65% by weight and preferably better still from 40 to 60% by weight with respect to the total weight of the composition. The surfactant system preferably comprises an amount of water-soluble soap(s) of at least 10% by weight with respect to the total weight of the composition and an overall amount of (water-soluble and insoluble) soaps preferably of at least 20% by weight with respect to the total weight of the composition and preferably ranging from 30 to 40% by weight with respect to the total weight of the composition.

The aqueous medium of the foaming creams of the invention can comprise, in addition to water, one or more solvents chosen from lower alcohols comprising from 1 to 6 carbon atoms, such as ethanol; polyols, such as glycerol; glycols, such as butylene glycol, isoprene glycol, propylene glycol or polyethylene glycols, such as PEG-8; sorbitol; sugars, such as glucose, fructose, maltose, lactose or sucrose; and their mixtures. The amount of solvent(s) in the composition of the invention can range from 0.5 to 30% by weight and preferably from 5 to 20% by weight with respect to the total weight of the composition.

To obtain more or less fluid compositions, one or more thickening agents, in particular polymers, can be incorporated in the compositions of the invention in concentrations preferably ranging from 0.05 to 2% by weight with respect to the total weight of the composition.

Mention may be made, as examples of thickeners, of:
polysaccharide biopolymers, such as xanthan gum, guar gum, alginates or modified celluloses;
synthetic polymers, such as polyacrylics, for example Carbopol 980, sold by Goodrich, or acrylate/acrylonitrile copolymers, such as Hypan SS201, sold by Kingston;
inorganic thickeners, such as smectites or modified or unmodified hectorites, such as the Bentone products sold by Rheox, Laponite products sold by Southern Clay Products or the Veegum HS product sold by R. T. Vanderbilt;
their mixtures.

The compositions according to the invention constitute more or less fluid creams, the $|G^*|$ moduli of which have, at a temperature of 25° C., values ranging from $10^2$ to $10^5$ Pa and the loss angles $\delta$ of which range from 10 to 45° for frequencies ranging from $10^{-2}$ to 10 Hz.

$|G^*|$ and $\delta$ are viscoelastic parameters used to measure the physical properties of viscoelastic fluids, as explained in "An introduction to rheology" by H. A. Barnes, J. F. Hutton and K. Walters, pages 46 to 54 (published by Elsevier—1989).

$|G^*|$ is the modulus of the complex modulus $G^*$ and $\delta$ is the loss angle. G' and G" are the components of $G^*$: $G^* = G' + iG''$. G' and G" are respectively the storage modulus and the loss modulus and i is equal to $(-1)^{1/2}$. The components G' and G" of the complex modulus are obtained from the relationship between the oscillatory stress and the oscillatory strain.

The rheological measurements of $|G^*|$ and $\delta$ are generally made using a Haake RS150 rheometer at a temperature of 25° C. with measuring bodies possessing cone-plate geometry, the diameter of the cone and the size of the plate being 60 mm, and the angle of the cone being 2° and the gap between the cone and the plate being 0.1 mm.

To make dynamic measurements of visco-elasticity (oscillatory measurements), first the linear viscoelastic region is determined by subjecting the sample to oscillatory stresses of increasing amplitudes and of constant frequency. The moduli are recorded as a function of the amplitude of the stress or of the amplitude of the strain, in order to determine the limits of the linear viscoelastic region. After having identified the linear viscoelastic region, dynamic measurements are made in the linear viscoelastic zone for a constant strain value lying in the linear visco-elastic region and at variable frequency. The Haake RS150 rheometer can cover a range of frequencies varying from 0.01 to 10 Hz (i.e. 0.063 to 62.8 rad/sec).

The following relationships are derived from the values of the amplitudes of the stress $\tau_0$ and of the strain $\gamma_0$ and from the loss angle $\delta$:

$$|G^*| = \frac{\tau_0}{\gamma_0}$$
$$G' = |G^*| \cos \delta$$
$$G'' = |G^*| \sin \delta$$
$$G^* = G' + iG''$$

The compositions of the invention can also comprise adjuvants commonly used in the field of foaming cleaners, such as cationic polymers of the polyquaternium type, which contribute softness and creaminess to the foaming cream. These cationic polymers may preferably be chosen from the following polymers:

Polyquaternium 5, such as the product Merquat® 5 sold by Calgon ®;
Polyquaternium 6, such as the product Salcare® SC 30 sold by Ciba® and the product Merquat® 100 sold by Calgon®;
Polyquaternium 7, such as the products Merquat® S, Merquat® 2200 and Merquat® 550 sold by Calgon® and the product Salcare® SC 10 sold by Ciba®;
Polyquaternium 10, such as the product Polymer JR400 sold by Amerchol®;
Polyquaternium 11, such as the products Gafquat®755, Gadquat ® 755N and Guafquat® 734 sold by ISP;
Polyquaternium 15, such as the product Rohagit® KF 270 F sold by Rohm;
Polyquaternium 16, such as the products Luviquat® FC905, Luviquat® FC370, Luviquat® HM552 and Luviquat® FC550 sold by BASF;
Polyquaternium 22, such as the product Merquat® 280 sold by Calgon®;
Polyquaternium 28, such as the product Styleze™ CC10 sold by ISP;
Polyquaternium 39, such as the product Merquat® Plus 3330 sold by Calgon®;
Polyquaternium 44, such as the product Luviquat® Care sold by BASF®;
Polyquaternium 46, such as the product Luviquat® Hold sold by BASF®;
Polyquaternium 47, such as the product Merquat® 2001 sold by Calgon®.

Use may also be made, as cationic polymer, of cationic guars, such as the product Jaguar sold by Rhodia.

In addition, the compositions of the invention can comprise adjuvants commonly used in the cosmetic field chosen from oils, active agents, fragrances, preservatives, sequestering agents (EDTA), pigments, pearlescent agents, inorganic or organic fillers, such as talc, kaolin, silica powder or polyethylene powder, soluble dyes or sunscreen agents. The amounts of these various adjuvants are those conventionally used in the field under consideration, for example from 0.01 to 20% of the total weight of the composition. These adjuvants and their concentrations must be such that they do not modify the property desired for the composition of the invention.

As oils, may be used for example oils of plant origin (jojoba oil, avocado oil, sesame oil, sunflower oil, corn oil, soybean oil, safflower oil or grape pip oil), mineral oils (petroleum jelly, optionally hydrogenated isoparaffins), synthetic oils (isopropyl myristate, cetearyl octanoate, polyisobutylene, ethylhexyl palmitate or alkyl benzoates), volatile or non-volatile silicone oils such as polydimethylsiloxanes (PDMSs) and cyclodimethylsiloxanes or cyclomethicones, and fluoro oils or fluorosilicone oils, as well as mixtures of these oils. The amount of oils must not modify the property desired for the composition of the invention: it is at most 15% of the total weight of the composition and preferably at most 10% of the total weight of the composition, and it is preferably from 0,1 to 5% of the total weight of the composition and preferably better still from 0,1 to 3% of the total weight of the composition.

Active agents which may be mentioned include for example moisturizers and, for example, protein hydrolysates and polyols such as glycerol, glycols, for instance polyethylene glycols, and sugar derivatives; natural extracts; procyannidol oligomers; vitamins; urea; caffeine; depigmenting agents such as kojic acid and caffeic acid; α-hydroxy acids such as lactic acid and glycolic acid; retinoids; screening agents; extracts of algae, of fungi, of plants, of yeasts or of bacteria; hydrolysed, partially hydrolysed or nonhydrolysed proteins, enzymes, co-enzyme Q10 or ubiquinone, hormones, vitamins and their derivatives, flavonoides and isoflavones, and mixtures thereof.

The compositions according to the invention can constitute in particular foaming creams for topical application used in particular in the cosmetic or dermatological fields as products for cleaning or removing make-up from the skin (body or face, including eyes), scalp and/or hair. A composition for topical use comprises a physiologically acceptable medium, that is to say compatible with the skin, mucous membranes, scalp, eyes and/or hair. The composition can constitute more particularly a composition for cleansing the skin.

Another subject-matter of the invention is the cosmetic use of the composition as defined above as products for cleaning and/or removing make-up from the skin, scalp and/or hair.

Another subject-matter of the invention is a cosmetic process for removing grime from the skin, scalp and/or hair, characterized in that the composition of the invention is applied to the skin, to the scalp and/or to the hair in the presence of water, in that it is massaged to form a foam and in that the foam foamed and the grime are removed by rinsing with water.

The examples which follow serve to illustrate the invention without, however, exhibiting a limiting nature. The amounts shown are in % by weight, unless otherwise mentioned.

EXAMPLE ACCORDING TO THE INVENTION

Foaming Cream for Cleansing the Skin

| | |
|---|---|
| Preservative | 0.4% |
| Tetrasodium EDTA | 0.2% |
| Potassium hydroxide | 7% |
| Glycerol | 7% |

-continued

| | |
|---|---|
| PEG-8 | 7% |
| Lauric acid | 3% |
| Myristic acid | 20% |
| Palmitic acid | 3% |
| Stearic acid | 3% |
| Glyceryl stearate (INCI name: Glyceryl stearate SE) | 5% |
| Cocoyl glucoside (comprising 50% of active material) (i.e. 1% of active material) | 2% |
| Water | qs. for 100% |

Procedure:

The aqueous phase, composed of the water-soluble ingredients (water, preservatives, EDTA, glycerol and PEG-8), is brought to 80° C. The fatty phase, composed of the fatty acids and of the glyceryl stearate is heated and added with stirring to the aqueous phase. The cocoyl glucoside is subsequently added and then the potassium hydroxide, dissolved in a portion of the water. Stirring is maintained for 10 minutes at 80° C. and then the combined mixture is cooled with stirring.

The obtained foaming composition is creamy and soft.

The water-soluble surfactants, composed of the potassium salts of lauric and myristic acids and of cocoyl glucoside, represent 29.5% of the composition, whereas the water-insoluble surfactants, composed of the potassium salts of palmitic and stearic acids and of glycerol stearate, represent 12.5% of the composition. The composition thus comprises a total of 42% of surfactants, including 36% of soaps (KOH+lauric, myristic, palmitic and stearic acids). The water-soluble soaps represent 28.5% of the weight of the composition.

The composition obtained has the appearance of a white cream at ambient temperature; it is converted into an extremely viscous translucent gel between 35 and 40° C.; this gel exists up to 75–80° C., at which temperature the composition fluidifies. On returning to ambient temperature of 25° C., this gel again has the appearance of a homogeneous cream.

This cream is perfectly stable at 4° C., at ambient temperature and at 45° C. for at least two months.

For this cream, the |G*| values are 2 900 Pa at 0.01 Hz and 25 000 Pa at 1 Hz, and the values of δ are 45° at 0.01 Hz and 40° at 1 Hz.

Characterization:

At 25° C., the cream is composed of a micellar phase which can be isolated by centrifuging (for one hour at 64 000 g, i.e. at 30 000 revolutions/minute, with a 3K30 Sigma centrifuge equipped with a 1210 rotor) and of a crystalline phase. The micellar phase is transparent, fluid and non-birefringent in polarized light or in X-ray diffraction. This phase results in a broad line at small angles centred around a distance d=49.8 Å and in a band at large angles centred around a distance d=4.64 Å.

On the basis of the measurements made on the complete cream, the crystalline phase exhibits a melting point: M.p.= 42° C. by DSC and is characterized in X-ray diffraction by 3 fine lines at small angles corresponding to distances d=42.7, 21.4 and 14.2 Å and 7 fine lines at large angles corresponding to d=4.37, 4.27, 4.19, 3.92, 3.68, 3.35 and 3.07 Å.

At 35° C., the cream is homogeneous at the macroscopic scale and is composed of a mixture of a hexagonal phase, characterized in X-ray diffraction by 2 fine lines at small angles corresponding to distances d=48.7 and 24.3 Å, and a crystalline phase characterized by 3 fine lines at small angles corresponding to d=42.0, 21.0 and 14.0 Å and 3 fine lines at large angles corresponding to d=4.29, 3.92 and 3.09 Å.

At 45° C., the cream is homogeneous at the macroscopic scale and is composed of a mixture comprising a hexagonal phase, characterized in X-ray diffraction by 2 fine lines at small angles corresponding to distances d=49.6 and 28.7 Å, and a fluid lamellar phase, characterized by 1 fine line at small angles corresponding to d=45.0 Å. At large angles, a band centred around 4.60 Å is observed, in agreement with the presence of paracrystalline phases.

At 55° C., the cream is homogeneous at the macroscopic scale and is composed of a mixture comprising a hexagonal phase, characterized in X-ray diffraction by 2 fine lines at small angles corresponding to distances d=47.7 and 27.5 Å, and a fluid lamellar phase, characterized by 1 weak fine line at small angles corresponding to d=36.5 Å. At large angles, a band centred around 4.70 Å is observed, in agreement with the presence of paracrystalline phases.

| Comparative example: | |
|---|---|
| Preservative | 0.4% |
| Tetrasodium EDTA | 0.2% |
| Potassium hydroxide | 4% |
| Glycerol | 7% |
| PEG-8 | 7% |
| Lauric acid | 3% |
| Myristic acid | 3% |
| Palmitic acid | 8.7% |
| Stearic acid | 8.7% |
| Glyceryl stearate (INCI name: Glyceryl stearate SE) | 0.75% |
| Sodium lauroyl sarcosinate (comprising 30% of active material) (approximately 7% of active material) | 21.8% |
| Water | qs. for 100% |

The procedure is the same as in Example 1.

The water-soluble surfactants, composed of the potassium salts of lauric and myristic acids and of sodium lauroyl sarcosinate, represent 14% of the composition, whereas the water-insoluble surfactants, composed of the potassium salts of palmitic and stearic acids and of glycerol stearate, represent 21.15% of the composition. The composition thus comprises 35.15% of surfactants, including 27.4% of soaps (KOH+lauric, myristic, palmitic and stearic acids). The water-soluble soaps represent 7% by weight of the composition.

The composition obtained has the appearance of a white cream at ambient temperature. This composition is very stable at 4° C. but it is unstable at 45° C., where it separates into two phases. When brought back to ambient temperature, it is heterogeneous.

At 25° C., the cream is composed of a micellar phase which can be isolated by centrifuging (for one hour at 64 000 g, i.e. 30 000 revolutions/minute with a 3K30 Sigma centrifuge equipped with a 1210 rotor) and of a crystalline phase.

The micellar phase is transparent, fluid and non-birefringent in polarized light. In X-ray diffraction, this phase results in a broad line at small angles centred around a distance d=50.0 Å and in a band at large angles centred around a distance d=4.53 Å.

On the basis of the measurements made on the complete cream, the crystalline phase exhibits a melting point: M.p.= 45° C. by DSC and is characterized in X-ray diffraction by fine lines at small angles corresponding to distances d=49.0, 24.1, 16.0, 12.2 and 9.64 Å and 6 fine lines at large angles corresponding to d=4.37, 4.28, 4.20, 3.94, 3.66 and 3.08 Å.

At 50° C., macroscopic demixing of the cream into two phases takes place: an upper phase of fluid lamellar type which exhibits, in polarized light, a characteristic texture of "Maltese Cross" type and results, in X-ray diffraction, in a fine line at small angles corresponding to 43.3 Å and in a band at large angles centred around 4.78 Å.

A lower phase of micellar solution type which is fluid, transparent and non-birefringent in polarized light and which is characterized, in X-ray diffraction, by a diffuse line at small angles corresponding to d=58.0 Å and a band at large angles centred around 4.80 Å.

The essential difference between the composition of the example according to the invention and the composition of the comparative example relates to the macroscopic appearance above 45° C.: the composition according to the invention gives a homogeneous system, whereas the composition of the comparative example results in demixing.

For the composition according to the invention of Example 1, the system is composed, above 45° C., of a lamellar phase as a mixture with a direct hexagonal phase, the high viscosity of which makes it possible to avoid macroscopic demixing.

For the composition of the comparative example, the system is composed, above 45° C., of a lamellar phase as a mixture with a micellar phase, the low viscosity of which does not make it possible to avoid macroscopic demixing, resulting in a heterogeneous composition after returning to ambient temperature.

Obviously, numerous modifications and variations of the present invention are possible in light of the above teachings. It is therefore to be understood that within the scope of the appended claims, the invention may be practiced otherwise than as specifically described herein.

What is claimed is:

1. A physiologically-acceptable composition comprising a surfactant system in an aqueous medium, wherein said surfactant system comprises at least 10% by weight water soluble soaps, and wherein said surfactant system exhibits at least one paracrystalline phase selected from the group consisting of direct hexagonal phase, cubic phase, and mixtures thereof, after the temperature increases above 30° C. and remains present up to at least 45° C.

2. The composition according to claim 1, wherein the paracrystalline phase is at least one direct hexagonal phase.

3. The composition according to claim 1, wherein said surfactant system further comprises a lamellar phase after the temperature increases above 30° C. which remains present up to at least 45° C.

4. The composition according to claim 1, wherein said composition has $|G^*|$ modulus ranging from $10^2$ to $10^5$ Pa at a temperature of 25° C. and a loss angle δ ranging from 10 to 45° for frequencies ranging from $10^{-2}$ to 10 Hz.

5. The composition according to claim 1 wherein the surfactant system comprises at least one water-soluble surfactant and at least one water-insoluble surfactant.

6. The composition according to claim 1, wherein the surfactant system comprises at least one water-soluble anionic surfactant.

7. The composition according to claim 6, wherein the water-soluble anionic surfactant is chosen from the group consisting of carboxylic acids and their salts, ethoxylated carboxylic acids and their salts, sarcosinates and acylsarcosinates and their salts, taurates and methyltaurates and their salts, isethionates and acylisethionates and their salts, sulphosuccinates and their salts, alkyl sulphates and alkyl ether sulphates and their salts, monoalkyl and dialkyl esters of phosphoric acid and their salts, alkanesulphonates and their salts, bile salts, lipoamino acids and their salts, geminal surfactants and their mixtures.

8. The composition according to claim 5, wherein the water-soluble surfactant is an amphoteric or zwitterionic surfactant chosen from the group consisting of betaines, sulphobetaines, alkylamphoacetates and their mixtures.

9. The composition according to claim 5, wherein the water-soluble surfactant is a nonionic surfactant chosen from the group consisting of polyol ethers, polyglycerol ethers and esters, polyoxyethylenated fatty alcohols, alkyl-$C_1$–$C_{14}$ polyglucosides, alkyl glucopyranosides and alkyl thioglucopyranosides, alkyl maltosides, alkyl-N-methylglucamides, polyoxyethylenated sorbitan esters, aminoalcohol esters and their mixtures.

10. The composition according to claim 5, wherein the water-insoluble surfactant is chosen from the group consisting of carboxylic acids and their salt, esters of glycerol and fatty acids, alkyl-$C_{15}$–$C_{30}$ polyglucosides, optionally oxyethylenated sterol and phytosterol derivatives, alkaline salts of cholesterol sulphate, alkaline salts of cholesterol phosphate, polyoxyethylenated fatty alcohols, dialkyl phosphates, lecithins, sphingomyelins, ceramides and their mixtures.

11. The composition according to claim 1, wherein the surfactant system is present in an amount, as active material, ranging from 20 to 65% by weight with respect to the total weight of the composition.

12. The composition according to claim 1, wherein the surfactant system comprises from 10 to 50% by weight of water-soluble surfactant with respect to the total weight of the composition.

13. The composition according to claim 1, wherein the surfactant system comprises at least 15% by weight of water-soluble surfactant with respect to the total weight of the composition.

14. The composition according to claim 1, wherein the surfactant system comprises from 30 to 40% by weight of water-soluble soap with respect to the total weight of the composition.

15. The composition according to claim 1, wherein the surfactant system comprises from 5 to 50% by weight of water-insoluble surfactant with respect to the total weight of the composition.

16. The composition according to claim 1, wherein the surfactant system comprises an overall amount of soaps of at least 20% by weight with respect to the total weight of the composition.

17. The composition according to claim 1, further comprising at least one solvent chosen from the group consisting of lower alcohols, polyols, sugars and their mixtures.

18. The composition according to claim 1, further comprising at least one thickening agent.

19. The composition according to claim 1, wherein said surfactant system exhibits at least one paracrystalline phase selected from the group consisting of direct hexagonal phase, cubic phase, and mixtures thereof, at temperatures above 45° C.

20. A process for cleansing grime from skin, scalp or hair comprising:

applying to the skin, scalp or hair a physiologically-acceptable composition comprising a surfactant system in an aqueous medium, wherein said surfactant system comprises at least 10% by weight of water soluble soaps, and wherein said surfactant system exhibits at least one paracrystalline phase selected from the group consisting of direct hexagonal phase, cubic phase, and mixtures thereof, after the temperature increases above 30° C. and remains present up to at least 45° C.;

forming a foam of said surfactant system by a massaging action; and rinsing said foam with water.

21. A process for cleansing skin, scalp or hair comprising:

applying to the skin, scalp or hair a physiologically-acceptable composition comprising a surfactant system in an aqueous medium, wherein said surfactant system comprises at least 10% by weight of water soluble soaps, and wherein said surfactant system exhibits at least one paracrystalline phase selected from the group consisting of direct hexagonal phase, cubic phase, and mixtures thereof, after the temperature increases above 30° C. and remains present up to at least 45° C.;

forming a foam of said surfactant system by a massaging action; and rinsing said foam with water.

22. The process according to claim 21, wherein said composition is a foaming cream composition.

23. The process according to claim 21, wherein said surfactant system exhibits a cubic phase after the temperature increases above 30° C. and remains present up to at least 45° C.

24. The composition according to claim 1, wherein said composition is a foaming cream composition.

25. The composition according to claim 1, wherein said surfactant system exhibits a cubic phase after the temperature increases above 30° C. and remains present up to at least 45° C.

26. The process according to claim 20, wherein said composition is a foaming cream composition.

27. The process according to claim 20, wherein said surfactant system exhibits a pubic phase when the temperature increases above 30° C. and remains present up to at least 45° C.

* * * * *

UNITED STATES PATENT AND TRADEMARK OFFICE
CERTIFICATE OF CORRECTION

PATENT NO. : 6,733,765 B2 Page 1 of 1
DATED : May 11, 2004
INVENTOR(S) : Veronique Guillou et al.

It is certified that error appears in the above-identified patent and that said Letters Patent is hereby corrected as shown below:

Column 16,
Line 14, "pubic" should read -- cubic --.

Signed and Sealed this

Twenty-third Day of November, 2004

JON W. DUDAS
*Director of the United States Patent and Trademark Office*